United States Patent [19]

Sansonetti et al.

[11] Patent Number: 4,992,364
[45] Date of Patent: Feb. 12, 1991

[54] PROBE FOR DNA AND A PROCESS FOR THE DETECTION OF "SHIGELLAE" AND ENTERO-INVASIVE STRAINS OF *ESCHERICHIA COLI*

[75] Inventors: Philippe Sansonetti; Catherine Boileau; Hélène D'Hauteville, all of Paris, France

[73] Assignees: Institut Pasteur; Institut National de la Sante et de la Recherche Medicale, both of Paris, France

[21] Appl. No.: 295,511

[22] Filed: Jan. 11, 1989

Related U.S. Application Data

[62] Division of Ser. No. 755,051, Jul. 12, 1985, Pat. No. 4,816,389.

[30] Foreign Application Priority Data

Jul. 13, 1984 [FR] France ............................ 84 11187

[51] Int. Cl.⁵ ..................... C12Q 1/68; C12P 19/34; C07H 21/04
[52] U.S. Cl. ........................................ 435/6; 435/29; 435/172.3; 435/320.1; 435/810; 436/501; 436/808; 536/27; 935/29; 935/78
[58] Field of Search .................. 435/6, 29, 172.3, 320, 435/810; 436/501, 808; 536/27; 935/29, 78

[56] References Cited

U.S. PATENT DOCUMENTS 4,358,535 11/1982 Falkow et al. .......................... 435/5
4,816,389 3/1989 Sansonetti et al. .................... 435/6

*Primary Examiner*—Robert A. Wax
*Assistant Examiner*—Ardin H. Marschel
*Attorney, Agent, or Firm*—Finnegan, Henderson, Farabow, Garrett & Dunner

[57] ABSTRACT

The invention concerns a probe for the detection of shigellae and entero-invasive *E. coli*, containing a nucleic acid sequence originating from the 140 Mdal virulence plasmid of the M 90 T strain of *Shigella flexneri*; having a maximum size of around 27 kb and including all or part of the 27 kb Bam HI fragment.

This probe permits the in vitro diagnosis of syndromes of dysentery or diarrhea, of the Shigellosis type.

11 Claims, 1 Drawing Sheet

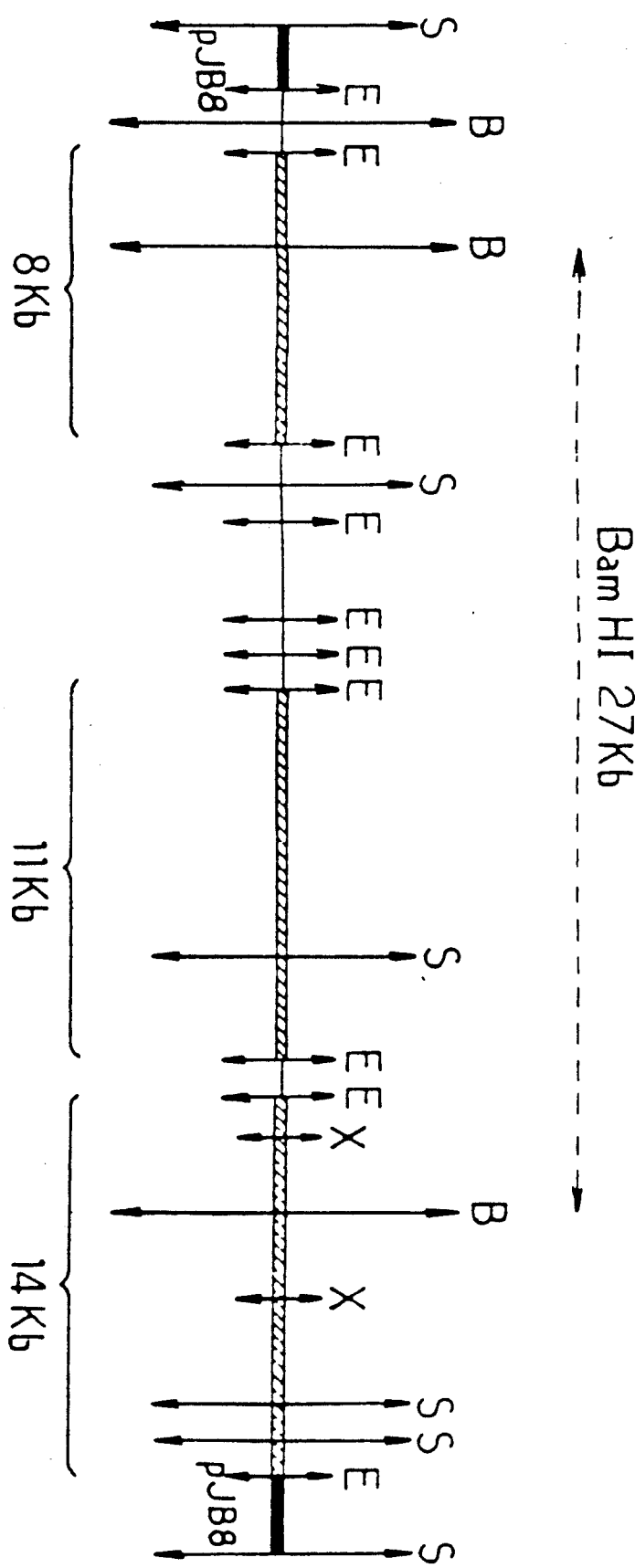

PROBE FOR DNA AND A PROCESS FOR THE DETECTION OF "SHIGELLAE" AND ENTERO-INVASIVE STRAINS OF *ESCHERICHIA COLI*

This is a division of application Ser. No. 755,051, filed July 12, 1985, now U.S. Pat. No. 4,816,389 issued Mar. 28, 1989.

BACKGROUND OF THE INVENTION

The invention concerns a process and the means, specifically a probe for DNA, for the detection of shigellae and entero-invasive strains of *E. coli*. It concerns more particularly, since it is in this case that it appears most promising, the means permitting in vitro diagnosis of the syndromes of dysenteries and diarrheas due to the kinds of bacteria in question whose capacity to invade the mucus cells of the colon and cause tissue damage, is well known. In a general manner, these afflictions will be hereafter referred to as shigelloses, whether they are actually due to shigellae or again to entero-invasive strains of *E. coli* which are nonetheless known to produce a dysentery of a similar type to those produced by the shigellae. It has, in addition, been noted that these strains of *E. coli* belong to various O serotypes which often give rise to cross-reactions with the A, B, and C serogroups of shigellae.

Shigelloses are endemic throughout the world. However, they present a particularly serious public health problem in tropical regions and developing countries where *Shigella dysenteriae* and *S. flexneri* predominate. In industralized countries, the principal etiologic agent is *S. sonnei* although sporadic cases of shigellosis are encountered due to *S. flexneri, S. boydii* and the above-mentioned serotype of entero-invasive *E. coli*.

The severity of dysenteric syndromes calls for rapid diagnosis and treatment of the disease. The detection of the bacterial species needs also to depend on rapid, simple and low-cost procedures. Unfortunately, no such procedure is currently available. The processes for the identification of the bacterial species responsible imply relatively complicated tests for bacteriological or immunological virulence. One of these tests involves the induction of a kerato-conjunctivitis in a guinea pig by the virulent bacteria (Sereny, B., Acta Microbiol. Hung. 4:367–376 (1957). Another test sometimes used involves in vitro colonization by these bacterial of mono-layers of human Hela cells in culture according to the technique described by Hale, et al., Infect. Immun., 32:137–144 (1981). It is obvious that these techniques are impractical for large-scale use for prevention or therapy.

SUMMARY OF THE INVENTION

The invention is the result of research leading to the isolation of genetic probes permitting a diagnosis based on selective hybridizations with nucleic acids previously isolated or rendered accessible from bacterial isolates and independent of the particular bacterial species of shigellae or entero-invasive *E. coli* responsible for the affliction.

It is known that all virulent strains of shigellae or entero-invasive *E. coli* harbor a plasmid of high molecular weight (120–140 megadaltons (1 Mdal = $10^6$ daltons), a plasmid which has proved to be indispensible to a fundamental step in the pathogenic power of these bacteria, that is, their capacity to penetrate epithelial cells.

In particular, Sansonetti, et al., (Infect. Immun., 35:852–860 (1982)) demonstrated that the virulence of one strain, M 90 T (serotype 5) was linked to the presence of a plasmid of 140 Mdal. This plasmid (pWR 110) was marked by a transposon (Tn5) which is resistant to kanamycin (the marked plasmid now pWR 110); those authors showed that the loss of this plasmid from the virulent strains of *S. flexneri*, for example, by incubation of cultures of these strains at 42° C. also cause loss of virulence. The production of major deletions of the plasmid again caused the same effects.

In a later article, Sansonetti, et al., (Ann. Microbiol. de l'Institut Pasteur, 134A:295–318 (1983)) definitely established the intervention of a plasmid of this type, in other words, of an extra-chromosomic element, in the virulence of all the entero-invasive strains belonging to the genus Shigella and *Escherichia coli*. However, if the experiments of crossed hybridization between the plasmids obtained from different species of Shigella or *E. coli* showed homologous sequences distributed over the ensemble of these plasmids, it was equally noted that from one species to another, the profiles of cleavages by restriction endonucleases, notably BamHI, EcoRI, etc, showed no obvious commonality. In addition, these authors found that the 140 Mdal plasmid they were using as a probe in their studies (virulence plasmid 4 605-58 from entero-invasive *E. coli*) hybridized not only with virulence plasmids from other strains, but also with other plasmids, notably smaller ones present in virulent as well as non-virulent strains. These findings then would seem to run counter to those which form the basis of the present invention, with particular sequences isolated from the 140 Mdal plasmid of the M 90 T strain of *S. flexneri* (serotype 5), sequences which proved to have such a selectivity that their use permits the discrimination, with a certainty close to 100% if not total, of shigellae or virulent strains of entero-invasive *E. coli* from bacterial isolates, notably those obtained from diarrheic stools.

The probe according to the invention for the detection of shigellae and entero-invasive *E. coli* is characterized in that it includes a nucleic acid sequence originating from the 140 Mdal virulence plasmid of the M 90 T strain of *Shigella flexneri*, having a maximum size of around 27 kb and containing all or a part of the BamHI fragment of 27 kb which can be isolated from the aforementioned virulence plasmid.

BRIEF DESCRIPTION OF THE DRAWINGS

This invention will be more fully understood by reference to the drawing in which:

The FIGURE shows a 45 kb fragment of pJB8 cosmid (in thick black lines) and three EcoRI fragments (in hatched lines) of 7.6 kb, 11.5 kb, and 14 kb.

DETAILED DESCRIPTION

Those probes particularly preferred are constituted of EcoRI sequences having, respectively, sizes of the order of 7.6 kb, 11.5 kb and 17 kb, these sequences having at least one part in common with the above-mentioned BamHI fragment of 27 kb. These apparent molecular weights were extrapolated using the restriction fragments obtained by the action of EcoRI and HindIII on the phage λ as a means of reference.

The reference fragments and the fragments of the present invention were separated by electrophoresis on a 0.7% agarose gel in buffer E (Kado, et al., J. of Bacteriology, 145:1365–1395 (1981)).

It is understood that in that which precedes "BamHI fragment" of 27 kb signifies the fragment which may be isolated from the 140 Mdal plasmid isolatable (notably by the method of Casse, et al., J. Gen. Microbiol., 113:229-242 (1979)) from the afore-mentioned M 90 T strain of S. flexneri, by treatment of this plasmid with the restriction enzyme BamHI and separation from the fragments those whose size is of the order of 27 kb. In the same way, the expression "EcoRI fragments" refers to those fragments which may be obtained from a larger plasmid, by fragmentation of it by the restriction enzyme EcoRI and subsequent recovery of the said restriction fragments.

It is also intended that in the definitions which precede the indication that the probes of the invention include "a part of the BamHI fragment of 27 kb" refers to the fact that these probes possess a part in common with this BamHI fragment or possessed such a part in common, in the case where subsequent deletions practiced on the fragments in question would have had for effect the elimination of the parts in common. These definitions naturally extend more particularly to the EcoRI fragments (intact) which, before the afore-mentioned deletions, included a part close to one or the other BamHI ends of the said BamHI fragment of 27 kb.

The preceding definitions extend equally to any DNA sequence obtained from a virulence plasmid from another species of shigella or from any of the entero-invasive E. coli insofar as these sequences give rise to a selective hybridization with the preferred sequences obtained from the 140 Mdal plasmid from the M 90 T strain of S. flexneri.

For the studies which have led to the invention, the M 90 T strain of S. flexneri serotype 5 (deposited with the National Collection of Cultures of Micro-organisms (CNCM) of the Institut Pasteur, the 6th of June 1984 under the number (No.) I-308) containing the 140 Mdal virulence plasmid pWR 100, was used. This strain presents the following characteristics: it is lactose $^-$, $Km^S$ (sensitive to kanamycin) and vir$^+$ (virulent).

The insertion in vivo of the transposon Tn5, which possesses a resistance factor $Km^r$, into the plasmid pWR 100, was resorted to.

To do this, first the plasmid F'$_{TS}$lac 114::Tn5 from the E. coli strain C 600 MU 735 (deposited with CNCM under the No I-307) coding for lactose and for kanamycin resistance due to the presence of Tn5, was transferred by bacterial conjugation into the virulent strain of M 90 T. The replication of this plasmid is thermo-sensitive and it may be lost by culturing at 42° C. after transposition.

The incorporation of the plasmid F'$_{TS}$lac 114::Tn5 into the strain M 90 T confers upon it the following characteristics:

Lactose$^+$, $Km^r$, Vir$^+$.

The transposition of Tn5 to the interior of plasmid pWR 100 in a gene sequence non-essential to the expression of the virulence of the strain M 90 T, does not modify the phenotype of the bacteria in question; but these transformed bacteria lose the plasmid F'$_{TS}$lac 114::Tn5 by incubation at 42° C.

After the loss of this plasmid, two categories of strains may be isolated from among $Km^r$ strains which have retained the plasmid pWR 100 (intact and non-deleted), presenting the phenotypes:

lactose$^-$, $Km^r$, vir$^+$ lactose$^-$, $Km^r$, vir$^-$ according to whether the transposon has been incorporated into a site essential or not to the manifestation of the virulence.

The presence of the transposon Tn5 in the plasmid or in the plasmids pWr 100::Tn5 is discerned by hybridization using as a probe a radio-actively marked sequence of 3200 base pairs belonging to Tn5.

Of a bank of 1000 clones tested, only 12 appeared to correspond to all of these requirements. The modified pWR 100::Tn5 plasmids were isolated from lactose$^-$, $Km^r$ and vir$^-$ strains and fragmented by the restriction enzyme EcoRI.

Starting from the restriction by EcoRI, the Tn5 inactivating the virulence proved to be systematically inserted into one of these three followed fragments (there exist 19 EcoRI fragments of pWR 100):
7.6 kb
11.5 kb
17 kb This has been confirmed by modification of the size of these fragments and hybridization with the Tn5 probe already mentioned. The corresponding EcoRI fragments isolated from the same plasmid EcoRI restriction, were then cloned into the EcoRI site of pBR 325 prepared from the E. coli strain HB 101 deposited at CNCM under the No I-306.

The following plasmids: pHS 3188 (7.6 kb), pHS 4011 (11.5 kb) and pHS 4033 (17 kb) were obtained.

The same conclusions were attained by another approach which consisted of cloning onto the cosmid pJB8, the plasmid sequences necessary to intra-cellular penetration. These sequences reside on the inserts of around 45 kb obtained from a pWR 100 plasmid.

Specifically, from one of the invasive clones pHS 4108 thus obtained, was isolated a fragment of 45 kb originating from the pWR 100 plasmid and recognized by its hybridization with a BamHI fragment of 27 kb as defined above. The restriction map of this 45 fragment is shown in FIG. 1. Thereon is also indicated the relative position of the 27 kb BamHI fragment used as a probe in addition to the different restriction sites which have been recognized.

The lone FIGURE also shows on either side of the 45 kb fragment the parts of the pJB 8 cosmid (in thick black lines) initially used and three EcoRI fragments (in hatched lines) of 7.6 kb, 11.5 kb and 14 kb which proved to hybridize respectively with the 7.6, 11.5, 17 kb fragments identified by the first method.

The different restriction sites are designated on the FIGURE by the restriction enzymes that correspond to them. It should be noted that the 14 kb fragment essentially corresponds to the 17 kb fragment isolated by the first method.

The three EcoRI fragments thus identified and isolated have been, like the 27 kb BamHI fragment, tested for their selective hybridization capacity with nucleic acids isolated from hundreds of virulent strains of shigella and entero-invasive E. coli. By contrast, they proved to have no hybridization capacity with shigellae or entero-invasive Escherichia coli inactivated by loss of the virulence plasmid or its deletion from genetic sequences necessary to intra-cellular penetration. These fragments are also unable to hybridize with nucleic acid compositions derived from other bacterial species. Examples of such bacteria will be cited further on in the context of the description of the tests for selectivity of these various fragments.

It results then from the above that the EcoRI fragments having sizes of the order of 7.6 kb, the order of 11.5 kb and the order of 17 kb possess a sequence, at least partial, in common with those of the 27 kb BamHI fragment which has been defined above.

The 7.6 kb fragment presents a particular interest. It has been observed that the avirulent cultures of shigellae transformed with the plasmid pHS 3188 (containing the 7.6 kb fragment) expressed a surface protein having a molecular mass of the order of 23,000 Dal. This protein is no longer expressed if the plasmid pHS 3188 containing the 7.6 kb EcoRI fragment into which Tn5 has been inserted is used for the transformation. This protein appears to be similar to the protein of around 23,000 Dal which may be detected at the surface of virulent strains of shigellae, a protein whose expression however is repressed when the strain is inactivated by culture at 30° C.

The EcoRI sequence of around 7.6 kb thus appears to be particularly critical for the expression of virulence. It contains one or more genes essential to the manifestation of the invasive power of virulent bacteria. The EcoRI fragments which may be easily isolated from a larger fragment coming from pWR 100 and capable of hybridizing with the 27 kb BamHI fragment, are of particular interest, not only because of their selectivity, but also their smaller size which allows them to be cloned in the current plasmids such as pBR 325, thus to amplify them.

The great selectivity of these diverse fragments conforming to the invention has been established by operating under the conditions which will be described hereafter.

Preparation and labeling of the DNA probe

The virulence plasmid was extracted from a culture of *S. flexneri* strain M 90 T as described in the article by Sansonetti, et al., in the 'Ann. Microbiol. de l'Institut Pasteur', 134A:295-318 (1983). The final purification was performed in a cesium chloride gradient. The BamHI restriction fragments of the virulence plasmid were then obtained by treatment of this latter with the enzyme BamHI according to the directions of the manufacturer (BOEHRINGER, Mannheim, Germany). These fragments were separated by electrophoresis on a low melting point vertical gel of 0.7% agarose (sold by B.R.L. of Gaithersburg, Md., U.S.A.) at 40 volts for 16 hours. The 27 kb BamHI fragment containing the sequences necessary for intra-cellular penetration was then recovered from the band of gel containing it by melting at 65° C. and dissolving in a small volume of buffer E (TRIS 0.05M, EDTA 0.02M, pH 8.0). The DNA was then extracted with phenol, precipitated by sodium acetate and alcohol at $-20°$ C., centrifuged and re-suspended in buffer E. Around 500 ng of the DNA thus obtained was radioactively labeled by the techniques called "Nick translation" with $^{32}P$-labeled nucleotides (AMERSHAM INTERNATIONAL), according to the technique described by Rigby, et al., J. Mol. Biol., 113:237-251 (1977). A probe having an activity of $6 \times 10^6$ to $10 \times 10^6$ cpm/$\mu$g of DNA was thus obtained.

This probe has been used to detect shigellae or entero-invasive *E. coli* under conditions which will be described further on. They have equally been used as probes to find and isolate EcoRI fragments having molecular weights of the order of 7.6 kb, 11.5 kb and 17 kb respectively, obtained by treatment of the same virulence plasmid by the restriction enzyme EcoRI, under conditions approximately analogous to those indicated above. These EcoRI fragments were also radioactively labeled under similar conditions.

Preparation of the stool samples

Stools obtained from patients with dysentery and from control subjects were treated with a view to their deposition on nitrocellulose filters for the hybridization assays. These stools were suspended in an appropriate volume of distilled water. The dilutions obtained were deposited on nitrocellulose filters prepared as described below.

Preparation of the nitrocellulose filters

The bacteria were cultured overnight at 37° C. in peptonized water (containing 5 g/l of NaCl and 20 g/l of indole-free peptone). Small quantities of the culture or of stools were deposited on a filter of nitrocellulose (BA 85, SCHLEICHER SCHUEL, Dassel, Germany) itself placed on the surface of a plate of Mac-CONKEYs agar. Twenty different strains were deposited on the filters in the same manner. After growing at 37° C., the bacteria were lysed and the DNA denatured as described by Moseley, et al., J. Infect. Dis., 142:892-898 (1980). The filters were placed for 10 minutes on WHATMAN No 3 paper saturated with 0.5M sodium hydroxide. Four transfers lasting one minute each were then carried out on paper saturated with 0.01M ammonium acetate and 0.02M sodium hydroxide. The filters were removed and carefully air dried, after a fifth transfer for 10 minutes onto ammonium acetate-sodium hydroxide saturated paper, before being subjected to a heat treatment overnight at 65° C. The filters thus treated were kept at room temperature.

Hybridization on the filters

The filters were incubated at 42° C. in a pre-hybridization solution (50% formamide, 5$\times$SSC (1$\times$SSC:0.15M NaCl; 0.015M sodium citrate), 5$\times$DENHARDTs solution, and 100 mg/ml of heat-denatured calf thymus DNA). The filters were then placed in sealed plastic bags containing 10 ml of the hybridization solution (50% formamide, 5$\times$SSC, 1$\times$DENHARDTs solution, dextran sulfate at 10%, 0.02M sodium phosphate pH 6.5), 100 $\mu$g/ml of calf thymus DNA and $10^6$ cpm of the DNA probe, both DNAs previously denatured by heat). Hybridization takes place overnight at 42° C. The filters are then washed as follows: three rinses of 5 minutes each in 2$\times$SSC and 0.01% SDS, then two times 30 minutes at 50° C. in 0.1$\times$SSC and 0.1% SDS. The filters were air dried before being exposed for 6 hours at $-70°$ C. to KODAK X-OMAT ® placed between two intensification screens (PHILIPS FRANCE). The film was then developed according to manufacturers instructions.

The different probes according to the invention have been used on hundreds of shigellae and entero-invasive *E. coli*. The control assays were done with extracts of Enterobacteriaceae, among which such entero-invasive bacteria as the Salmonellae and Yersiniae. Other gram-negative were equally tested, among which such causative agents of diarrheas as the Vibrios and Plesiomonas.

The assays were also done on control shigellae and the entero-invasive *E. coli* having lost their virulence plasmids. The assays were performed on several types of shigellae, notably *S. sonnei, S. flexneri, S. boydi* and *S. dysenteriae*. Over 300 shigella isolates were assayed.

The results of the hybridization assays showed that the sensitivity of the method was 99.7% and the specificity 100%. At most one observes certain variations in the intensity of the autoradiograms obtained with virulent colonies of *S. sonnei*, perhaps because of the known increased instability of their virulence plasmids. Practically no hybridization was obtained with the DNA of the control bacteria (those of other species or of shigellae or entero-invasive *E. coli* whose virulence plasmids were either lost or 'engineered' with inactivating deletions).

The quantitative assays (according to the bacterial content of the dilutions initially deposited on the nitrocellulose filters) showed that the probes according to the invention could detect $10^3$ colony-forming units (C.F.U.) of shigellae, that is dilutions 10 to 100 times greater than the maximum dilutions detected by previous bacteriologic procedures.

For the assays on diarrheic stool samples, the results of hybridization with the three types of probes (7.6, 11.5 and 17 kb) according to the invention permitted confirmation of the greatest sensitivity for the 17 kb probe in the diagnosis of shigellae.

In the preceding, the probes were radioactively labeled. Obviously the invention is not limited to this mode of labelling. In a manner known in itself, the probes may be modified with a chemical group permitting their coupling, directly or indirectly, for example, with an enzyme whose presence may be revealed by its action with regard to a specific substrate, preferably one that is chromogenic, or again with a molecule which is fluorescent of luminescent. Coupling methods of this type were in mind, for example, in French patents 78 10975 and 81 24631 or in the published European patent application 0063879.

The invention naturally concerns equally the detection process itself for virulent shigellae and entero-invasive *E. coli* using the probes corresponding to the invention. In a general fashion the principal steps of the detection process according to the invention include:

the deposition and fixation of the nucleic acids of the cells to be analyzed (or the cells themselves treated in such a manner as to permit access of their nucleic acids to the probe) onto an appropriate filter, such as one of nitrocellulose or analogue;

the bringing into contact the nucleic acids thus fixed or rendered accessible, with the labelled probe according to the invention under conditions permitting effective hybridization, when the bacteria being sought are present;

the elimination notably by washing, of any non-hybridized probe; and the detection of the probes for DNA retained by hybridization on the support.

The invention also naturally concerns the essential items of "Kits" containing a probe corresponding to the invention and, as the case may be, control preparations of stools samples, or of nucleic acids from non-virulent strains, and any other reagents necessary to the test.

However, the invention is not limited to the application of the probes of the invention to the challenge of in vitro diagnosis of shigelloses but may also be used in systematic screening for shigellae and entero-invasive *E. coli* in the normal environment of man, for example, in water, food, etc. It may also be used in analysis, notably for the classification of newly isolate virulent bacteria, according to whether their nucleic acids hybridize or not with the probes of the invention. And too it can be used to isolate complementary sequences from fragmented nucleic acids in the operations of selective hybridization. In such a case the nucleic acid sequences of the invention would be better attached in a way already known to an insoluble support. The support-borne probe is then put in contact with the nucleic acid solution presumed to contain fragments to be selected under conditions favorable to hybridization, the unfixed nucleic acids are removed and, after denaturation, the retained fragments are recovered from the hybrids which were formed.

And lastly, the DNA fragments of the invention, and especially the EcoRI fragment of around 7.6 kb, may be used in studies into the production of vaccines effective against shigellae, notably subject to its stable incorporation into a chromosome of a non-pathogenic *E. coli* under conditions which would permit the subject expression by the *E. coli* of this fragment, notably in the form having properties of the surface protein of 23,000 daltons discussed above.

As it goes without saying and as it results already from what precedes, the invention is in no way limited to those applications or modes of realization described herein, on the contrary, it embraces all variants.

In particular it is self-evident that the definitions contained in the claims should be considered as having a range equal to the definitions discussed in the description. The claims, of course, equally extend their effects most especially to any probe hybridizing with the preferred sequences which have been defined in the present patent application, but not hybridizing with nucleic acid sequences likely to be obtained from inactivated shigellae or entero-invasive *E. coli* or those stripped of their virulence. In particular these would be bacteria which still contain parts of the virulence plasmid but which however have had deleted the intra-gene sequences to which may be attributed the said virulence.

We claim:

1. A process for detecting in vitro the presence of cells of a virulent *Shigellae flexneri*, wherein the process comprises the steps of:
   (A) depositing and fixing nucleic acids of the cells on a filter, so as to make the nucleic acids accessible to a probe;
   (B) contacting said fixed nucleic acids from step (A) with the probe under conditions permitting hybridization;
   (C) washing said filter resulting from step (B), so as to eliminate any non-hybridized probe; and then
   (D) detecting any hybridized probe on said washed filter resulting from step (C);
   wherein said probe comprises a nucleic acid sequence which is present in a 140 Mdal virulence plasmid of a M 90 T strain of *Shigellae flexneri*, wherein said nucleic acid sequence has a maximum size of about 27 kb and the nucleic acid sequence includes all or part of a 27 kb BamHI fragment of said 140 Mdal plasmid and in addition, an 11.5 kb EcoRI fragment of said 140 Mdal plasmid, wherein said 11.5 kb fragment has a part in common with said 27 kb BamHI fragment.

2. A process for detecting in vitro the presence of cells of a virulent *Shigellae sonnei*, wherein the process comprises the steps of:

(A) depositing and fixing nucleic acids of the cells on a filter, so as to make the nucleic acids accessible to a probe;

(B) contacting said fixed nucleic acids from step (A) with a probe under conditions permitting hybridization;

(C) washing said filtrate resulting from step (B), so as to eliminate any non-hybridized probe; and then (D) detecting any hybridized probe on said washed filter resulting from step (C);

wherein said probe comprises a nucleic acid sequence which is present in a 140 Mdal virulence plasmid of a M 90 T strain of *Shigellae flexneri*, wherein the nucleic acid sequence has a maximum size of about 27 kb and the nucleic acid sequence includes all or part of a 27 kb BamHI fragment of said 140 Mdal plasmid and, in addition, an 11.5 kb EcoRI fragment of said 140 Mdal plasmid, wherein said 11.5 kb fragment has a part in common with 27 kb BamHI fragment.

3. A process for detecting in vitro the presence of cells of a virulent *Shigellae dysenteriae,* wherein the process comprises the steps of:

(A) depositing and fixing nucleic acids of the cells on a filter, so as to make the nucleic acids accessible to a probe;

(B) contacting said fixed nucleic acids from step (A) with a probe under conditions permitting hybridization;

(C) washing said filter resulting from step (B), so as to eliminate any non-hybridized probe; and then (D) detecting any hybridized probe on said washed filter resulting from step (C);

wherein said probe comprises a nucleic acid sequence which is present in a 140 Mdal virulence plasmid of a M 90 T strain of *Shigellae flexneri,* wherein said nucleic acid sequence has a maximum size of about 27 kb and the nucleic acid sequence includes all or part of a 27 kb BamHI fragment of said 140 Mdal plasmid and, in addition, an 11.5 kb EcoRI fragment of said 140 Mdal plasmid, wherein said 11.5 kb fragment has a part in common with said 27 kb BamHI fragment.

4. A process as claimed in claim 1, 2, or 3 wherein the probe has a label selected from the group consisting of radioactive, enzymatic, fluorescent, and luminescent labels.

5. A process for detecting in vitro the presence of cells of a virulent *Shigellae flexneri,* wherein the process comprises the steps of:

(A) depositing and fixing nucleic acids of the cells on a filter, so as to make the nucleic acids accessible to a probe;

(B) contacting said fixed nucleic acids from step (A) with a probe under conditions permitting hybridization;

(C) washing said filter resulting from step (B), so as to eliminate any non-hybridized probe; and then (D) detecting any hybridized probe on said washed filter resulting from step (C);

wherein said probe comprises a nucleic acid sequence which is present in a 140 Mdal virulence plasmid of a M 90 T strain of *Shigellae flexneri,* wherein said nucleic acid sequence has a maximum size of about 27 kb and the nucleic acid sequence includes all or part of a 27 kb BamHI fragment of said 140 Mdal plasmid and, in addition, a 7.6 kb EcoRI fragment of said 140 Mdal plasmid, wherein said 7.6 fragment has a part in common with said 27 kb BamHI fragment.

6. A process for detecting in vitro the presence of cells of a virulent *Shigellae boydii,* wherein the process comprises the steps of:

(A) depositing and fixing nucleic acids of the cells on a filter, so as to make the nucleic acids accessible to a probe;

(B) contacting said fixed nucleic acids from step (A) with a probe under conditions permitting hybridization;

(C) washing said filter resulting from step (B), so as to eliminate any non-hybridized probe; and then (D) detecting any hybridized probe on said washed filter resulting from step (C);

wherein said probe comprises a nucleic acid sequence which is present in a 140 Mdal virulence plasmid of a M 90 T strain of *Shigellae flexneri,* wherein said nucleic acid sequence has a maximum size of about 27 kb and the nucleic acid sequence includes all or part of a 27 kb BamHI fragment of said 140 Mdal plasmid and, in addition, a 7.6 kb EcoRI fragment of said 140 Mdal plasmid, wherein said 7.6 kb fragment has a part in common with said 27 kb BamHI fragment.

7. A process for detecting in vitro the presence of cells of a virulent *Shigellae dysenteriae,* wherein the process comprises the steps of:

(A) depositing and fixing nucleic acids of the cells on a filter, so as to make the nuclei acids accessible to a probe;

(B) contacting said fixed nucleic acids from step (A) with a probe under conditions permitting hybridization;

(C) washing said filter resulting from step (B), so as to eliminate any non-hybridized probe; and then (D) detecting any hybridized probe on said washed filter resulting from step (C);

wherein said probe comprises a nucleic acid sequence which is present in a 140 Mdal virulence plasmid of a M 90 T strain of *Shigellae flexneri,* wherein said nucleic acid sequence has a maximum size of about 27 kb and the nucleic acid sequence includes all or part of a 27 kb BamHI fragment of said 140 Mdal plasmid and, in addition, a 7.6 kb EcoRI fragment of said 140 Mdal plasmid, wherein said 7.6 kb fragment has a part in common with said 27 BamHI fragment.

8. A process for detecting in vitro the presence of cells of a virulent entero-invasive *Escherichia coli,* wherein the process comprises the steps of:

(A) depositing and fixing nucleic acids of the cells on a filter, so as to make the nucleic acids accessible to a probe;

(B) contacting said fixed nucleic acids from step (A) with a probe under conditions permitting hybridization;

(C) washing said filter resulting from step (B), so as to eliminate any non-hybridized probe; and then (D) detecting any hybridized probe on said washed filter resulting from step (C);

wherein said probe comprises a nucleic acid sequence which is present in a 140 Mdal virulence plasmid of a M 90 T strain of *Shigellae flexneri,* wherein said nucleic acid sequence has a maximum size of about 27 kb and the nucleic acid sequence includes all or part of a 27 kb BamHI fragment of said 140 Mdal plasmid and, in addition, a 7.6 EcoRI fragment of said 140 Mdal plasmid, wherein said 7.6 kb fragment has a part in common with said 27 kb BamHI fragment.

9. A process as claimed in claim 5, 6, 7, or 8, wherein the probe has a label selected from the group consisting of radioactive, enzymatic, fluorescent, and luminescent labels.

10. A kit for the detection of virulent Shigellae and entero-invasive *Escherichia coli* microorganisms, wherein the kit comprises:
(A) a container means containing a probe comprising a nucleic acid sequence which is present in a 140 Mdal virulence plasmid of a M 90 T strain of *Shigellae flexneri*, wherein said nucleic acid sequence has a maximum size of about 27 kb and the nucleic acid sequence includes all or part of a 27 kb BamHI fragment of said 140 Mdal plasmid and, in addition, an 11.5 kb EcoRI fragment or a 7.6 kb EcoRI fragment of said 140 Mdal plasmid, wherein said 11.5 kb fragment and said 7.6 kb fragment have a part in common with said BamHI fragment; and
(B) a container means containing a control preparation of nucleic acid of an avirulent strain of a microorganism or of nucleic acid of a stool from a healthy individual.

11. A kit as claimed in claim 10, wherein the probe has a label selected from the group consisting of radioactive, enzymatic, fluorescent, and luminescent labels.

* * * * *